US011413222B2

(12) United States Patent
Sato et al.

(10) Patent No.: US 11,413,222 B2
(45) Date of Patent: Aug. 16, 2022

(54) DENTAL POLYMERIZABLE COMPOSITION

(71) Applicant: GC Corporation, Shizuoka (JP)

(72) Inventors: Keita Sato, Tokyo (JP); Shogo Murakami, Tokyo (JP); Hiroaki Kakinuma, Tokyo (JP)

(73) Assignee: GC Corporation, Shizuoka (JP)

(*) Notice: Subject to any disclaimer, the term of this patent is extended or adjusted under 35 U.S.C. 154(b) by 0 days.

(21) Appl. No.: 17/197,310

(22) Filed: Mar. 10, 2021

(65) Prior Publication Data
US 2021/0298999 A1 Sep. 30, 2021

(30) Foreign Application Priority Data

Mar. 24, 2020 (JP) .............................. JP2020-053185

(51) Int. Cl.
*A61K 6/887* (2020.01)
*A61K 6/77* (2020.01)
(52) U.S. Cl.
CPC ................. *A61K 6/887* (2020.01); *A61K 6/77* (2020.01)
(58) Field of Classification Search
CPC combination set(s) only.
See application file for complete search history.

(56) References Cited

U.S. PATENT DOCUMENTS

| 2010/0249266 | A1* | 9/2010 | Yarimizu | A61K 6/887 |
| | | | | 523/116 |
| 2010/0311864 | A1* | 12/2010 | Arita | A61K 6/84 |
| | | | | 523/105 |
| 2012/0059083 | A1* | 3/2012 | Tokui | A61K 6/30 |
| | | | | 526/147 |
| 2016/0051450 | A1* | 2/2016 | Kashiki | A61K 6/60 |
| | | | | 526/204 |
| 2018/0110683 | A1* | 4/2018 | Yoshinaga | A61K 6/62 |
| 2019/0008730 | A1* | 1/2019 | Fujimi | A61K 6/62 |

FOREIGN PATENT DOCUMENTS

| EP | 2258336 | 12/2010 |
| EP | 3156032 | 4/2017 |
| JP | 2012-051856 | 3/2012 |

* cited by examiner

Primary Examiner — Peter A Salamon
(74) Attorney, Agent, or Firm — IPUSA, PLLC

(57) ABSTRACT

A dental polymerizable composition includes a first component containing a (meth)acrylate free of an acid group, a (meth)acrylate having a carboxyl group, a basic filler, and an organic peroxide; and a second component containing a (meth)acrylate free of an acid group, a vanadium compound, and a thiourea derivative.

12 Claims, No Drawings

DENTAL POLYMERIZABLE COMPOSITION

CROSS-REFERENCE TO RELATED APPLICATIONS

This application is based upon and claims priority to Japanese Patent Application No. 2020-053185, filed on Mar. 24, 2020, the entire contents of which are incorporated herein by reference.

FIELD OF THE INVENTION

The present invention relates to a dental polymerizable composition.

BACKGROUND OF THE INVENTION

Patent Document 1 discloses a polymerizable composition containing, for example, a first component including a (meth)acrylate and an organic peroxide, and a second component including a (meth)acrylate, a vanadium compound, and a thiourea derivative, wherein the polymerizable composition can be used under wet conditions such as in an oral cavity in a dental treatment.

RELATED-ART DOCUMENT

Patent Documents

Patent Document 1: Japanese Patent Application Laid-Open No. 2012-51856

SUMMARY OF THE INVENTION

Problems to be Solved by the Invention

The curability of the polymerizable composition described above may be improved by mixing a (meth)acylate having a phosphate group.

However, there is a problem that, for example, when basic fillers such as barium glass powders, which is capable of improving the X-ray contrast of a cured product, is added, the basic filler adsorbs the (meth)acrylate having a phosphate group, thereby reducing the storage stability of the polymerizable composition.

One aspect of the invention is to provide a dental polymerizable composition that exhibits improved curability and storage stability even if a dental polymerizable composition includes a basic filler.

Means for Solving the Problems

One aspect of the invention is a dental polymerizable composition containing a first component including a (meth)acrylate free of an acid group, a (meth)acrylate having a carboxyl group, a basic filler, and an organic peroxide; and a second component including a (meth)acrylate free of an acid group, a vanadium compound, and a thiourea derivative.

Effects of the Invention

One aspect of the invention is to provide a dental polymerizable composition that exhibits improved curability and storage stability even if a dental polymerizable composition includes a basic filler.

DETAILED DESCRIPTION OF THE INVENTION

Next, an embodiment for carrying out the present invention will be described.

<Dental Polymerizable Composition>

A dental polymerizable composition of the present invention contains a first component including a (meth)acrylate free of an acid group, a (meth)acrylate having a carboxyl group, a basic filler, and an organic peroxide; and a second component including a (meth)acrylate having free of an acid group, a vanadium compound, and a thiourea derivative.

In the present specification and claims, a (meth)acrylate refers to a compound (e.g., monomer, oligomer, prepolymer) having one or more methacryloyloxy groups and/or acryloyloxy groups (hereinafter referred to as (meth)acryloyloxy groups).

The second component may further include a basic filler. In this case, the basic filler included in the second component may be the same as or different from the basic filler included in the first component.

Examples of forms of the first component and the second component include a paste and the like.

The mass ratio of the first component and the second component of the dental polymerizable composition of the present embodiment is typically within the range of from 10:1 to 1:10.

The dental polymerizable composition of the present embodiment is typically used by kneading the first and second components.

The dental polymerizable composition of the present embodiment can be applied to dental cements and the like.

Hereinafter, components constituting a dental polymerizable composition of the present embodiment will be described.

<(Meth)Acrylate Free of an Acid Group>

The (meth)acrylate free of an acid group preferably has two or more (meth)acryloyloxy groups.

Examples of the (meth)acrylates free of an acid group include methyl (meth)acrylate, ethyl (meth)acrylate, isopropyl (meth)acrylate, n-butyl (meth)acrylate, isobutyl (meth)acrylate, hydroxypropyl (meth) acrylate, tetrahydrofurfuryl (meth) acrylate, glycidyl (meth) acrylate, 2-hydroxyethyl (meth) acrylate, 2-hydroxypropyl (meth) acrylate, 3-hydroxypropyl (meth) acrylate, 2-methoxyethyl (meth) acrylate, 2-ethoxyethyl (meth) acrylate, 2-methylhexyl (meth) acrylate, 2-ethylhexyl (meth) acrylate, benzyl (meth)acrylate, 2-hydroxy-1,3-di(meth)acryloyloxypropane, ethyleneglycol di(meth)acrylate, diethyleneglycol di(meth)acrylate, triethyleneglycol di(meth)acrylate, butyleneglycol di(meth)acrylate, neopentylglycol di(meth)acrylate, 1,3-butanediol di(meth)acrylate, 1,4-butanediol di(meth)acrylate, 1,6-hexanediol di(meth)acrylate, trimethylolpropane tri (meth)acrylate, trimethylolethane tri(meth)acrylate, pentaerythritol tri(meth)acrylate, trimethylolmethane tri(meth)acrylate, pentaerythritol tetra(meth)acrylate, polybutyleneglycol di(meth)acrylate, bisphenol-A diglycidyl (meth)acrylate, ethoxylated bisphenol-A di(meth)acrylate, di-2-(meth)acryloyloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H)triazine-2,4,6-trione, 2,2-bis[4-(3-(meth)acryloyloxy-2-hydroxypropyl)phenyl]propane, N,N'-(2,2,4-trimethylhexamethylene)bis[2-(aminocarboxy)propane-1,3-diol]tetramethacrylate, and the like. Two or more kinds of (meth)acrylates free of an acid group may be used in combination. Among these, di-2-(meth)acryloyloxyethyl-2, 2,4-trimethylhexamethylene dicarbamate, ethoxylated bisphenol-A di(meth)acrylate, neopentyl glycol di(meth)acrylate, and 2-hydroxy-1,3-di(meth)acryloyloxypropane are preferably used in terms of the mechanical strength of the cured product of the dental polymerizable composition of the present embodiment.

The content of the (meth)acrylate free of an acid group in the dental polymerizable composition of the present embodiment is preferably 10 to 95% by mass and further preferably 15 to 80% by mass, improving the workability with the dental polymerizable composition of the present embodiment when the content of the (meth)acrylate in the dental polymerizable composition of the present embodiment is 10% by mass or more and 95% by mass or less.

<(Meth)Acrylate having a Carboxyl Group>

The (meth)acrylate having a carboxyl group preferably has two or more carboxyl groups.

Alternatively, acid chlorides, alkali metal salts, and amine salts of (meth)acrylates having carboxyl groups may be used instead of (meth)acrylate having a carboxyl group.

Examples of the (meth)acrylates having carboxyl groups include 2-methacryloyloxyethyl succinic acid, (meth)acrylic acid, 4-(meth)acryloyloxyethyl trimellitic acid, 4-(meth)acryloyloxyethyl trimellitic anhydride, 4-(meth)acryloyloxy trimellitic acid, 4-(meth)acryloyloxydecyl trimellitic anhydride, 11-(meth)acryloyloxy-1,1-undecanedicarboxylic acid, 1,4-di(meth)acryloyloxy pyromellitic acid, 2-(meth) acryloyloxyethyl maleic acid, 2-(meth) acryloyloxyethyl phthalic acid, 2-(meth)acryloyloxyethyl hexahydrophthalic acid, and the like. Among these, 2-methacryloyl oxyethyl-succinic acid and (meth)acrylic acid are preferably used in terms of storage stability of the dental polymerizable composition of the present embodiment.

The (meth)acrylate having a carboxyl group may be used alone or in combination with two or more kinds.

The content of the (meth)acrylate having a carboxyl group in the dental polymerizable composition of the present embodiment is preferably 0.1 to 0.9% by mass and further preferably 0.2 to 0.8% by mass. When the content of (meth)acrylate having a carboxyl group in the dental polymerizable composition of the present embodiment is 0.1 to 0.9% by mass, improving the curability of the dental polymerizable composition of the present embodiment.

Also, for the same reason as above, the content of the (meth)acrylate having a carboxyl group in the first component is preferably 0.2 to 1.8% by mass and further preferably 0.4 to 1.6% by mass.

The dental polymerizable composition of the present embodiment preferably does not contain a (meth)acrylate having acid groups other than carboxyl groups (e.g., phosphate, pyrophosphate, thiophosphate, sulfonate, phosphonate). This improves the storage stability of the dental polymerizable composition of the present embodiment.

<Basic Filler>

A basic filler is preferably glass powders containing barium, strontium or lanthanum.

Examples of the glass powders containing barium, strontium, or lanthanum include barium glass powder, strontium glass powder, lanthanum glass powder, barium boroaluminosilicate glass powder, strontium boroaluminosilicate glass powder, lanthanum aluminosilicate glass powder, strontium fluoroaluminosilicate glass powder, barium fluoroaluminosilicate glass powder, lanthanum fluoroaluminosilicate glass powder, and the like. Two or more kinds of the glass powders containing barium, strontium, or lanthanum may be used in combination. Among these, barium glass powder is preferably used in terms of an X-ray contrast of a cured product of the dental polymerizable composition of the present embodiment.

The basic filler may be treated with a surface treatment agent such as a silane coupling agent and the like.

The content of the basic filler in the dental polymerizable composition of the present embodiment is preferably 4 to 90% by mass and further preferably 15 to 80% by mass. When the content of the basic filler in the dental polymerizable composition of the present embodiment is 4% by mass or more, improving the X-ray contrast of the cured product of the dental polymerizable composition of the present embodiment. When the content of the basic filler in the dental polymerizable composition of the present embodiment is 90% by mass, improving the workability of the dental polymerizable composition of the present embodiment.

<Organic Peroxides>

An organic peroxide functions as an oxidizer for a chemical polymerization initiator.

Examples of the organic peroxides include benzoyl peroxide, cumene hydroperoxide, t-butyl hydroperoxide, t-amyl hydroperoxide, 1,1,3,3-tetramethylbutyl hydroperoxide, 2,5-dimethyl-2,5-di(hydroperoxy)hexane, p-diisopropylbenzene monohydroperoxide, p-methane hydroperoxide, pinane hydroperoxide, and the like. Two or more kinds of the organic peroxides may be used in combination. Among these, cumene hydroperoxide is preferably used in terms of curability of the dental polymerizable composition of the present embodiment.

The content of the organic peroxide in the dental polymerizable composition of the present embodiment is preferably 0.01 to 5% by mass and further preferably 0.1 to by mass. When the content of the organic peroxide in the dental polymerizable composition of the present embodiment is 0.01% by mass or more and 5% by weight or less, improving the curability of the dental polymerizable composition of the present embodiment.

For the same reason as above, the content of the organic peroxide in a first component is preferably 0.02 to 10% by mass and further preferably 0.2 to 4% by mass.

<Vanadium Compound>

A vanadium compound functions as a polymerization accelerator.

Examples of the vanadium compounds include oxovanadium oxalate, vanadyl acetylacetonate, vanadium acetylacetonate, vanadyl stearate, vanadium naphthenate, vanadium benzoyl acetonate, and the like. Two or more kinds of the vanadium compounds may be used in combination. Among these, vanadyl acetylacetonate is preferably used in terms of curability of the dental polymerizable composition of the present embodiment.

The content of the vanadium compound in the dental polymerizable composition of the present embodiment is preferably from 0.001 to 1% by mass and further preferably from 0.002 to 0.1% by mass. When the content of the vanadium compound in the dental polymerizable composition of the present embodiment is 0.001% by mass or more, improving the curability of the dental polymerizable composition of the present embodiment. When the content of the vanadium compound in the dental polymerizable composition of the present embodiment is 1% by mass or less, improving the storage stability of the dental polymerizable composition of the present embodiment.

Also, for the same reasons as above, the content of the vanadium compound in a second component is preferably 0.002 to 2% by mass and further preferably 0.004 to 0.2% by mass.

<Thiourea Derivatives>

A thiourea derivative functions as a reducing agent of a chemical polymerization initiator.

Examples of the thiourea derivatives include ethylene thiourea, N-methylthiourea, N-ethylthiourea, N-propylthiourea, N-butylthiourea, N-lauryl thiourea, N-phenylthiourea, N-cyclohexylthiourea, N,N-dimethyl thiourea, N,N-diethylthiourea, N,N-dipropylthiourea, N,N-dibutylthiourea, N,N-dilauryl thiourea, N,N-diphenylthiourea, N,N-dicyclohexylthiourea, trimethylthiourea, tetramethyl thiourea, N-acetylthiourea, N-benzoyl thiourea, 1-allyl-3-(2-hydroxyethyl)-2-thiourea, 1-(2-tetrahydrofurfuryl)-2-thiourea, N-tert-butyl-N'-isopropylthiourea, 2-pyridylthiourea, and the like. Two or more kinds of the thiourea derivatives may be used in combination. Among these, N-benzoyl thiourea is preferably used in terms of curability of the dental polymerizable composition of the present embodiment.

The content of the thiourea derivative in the dental polymerizable composition of the present embodiment is preferably 0.1 to 5% by mass and further preferably 0.1 to 1% by mass. When the content of the thiourea derivative in the dental polymerizable composition of the present embodiment is 0.1% by mass or more, improving the curability of the dental polymerizable composition of the present embodiment. When the content of the thiourea derivative in the dental polymerizable composition of the present embodiment is 5% by mass or less, improving the solubility of the thiourea derivative in the dental polymerizable composition of the present embodiment with respect to (meth)acrylate.

Also, for the same reason as above, the content of the thiourea derivative in the second component is preferably 0.2 to 10% by mass and further preferably 0.2 to 2% by mass.

<Other Components>

The second component may further contain a tertiary amine.

The tertiary amine functions as a reducing agent in a chemical polymerization initiator.

The tertiary amine may be either a tertiary aliphatic amine or a tertiary aromatic amine, but is preferably a tertiary aromatic amine, particularly alkyl p-dialkylaminobenzoate.

The tertiary aliphatic amines include, for example, N,N-dimethylaminoethylmethacrylate, triethanolamine, and the like.

Examples of the alkyl p-dialkylaminobenzoates include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, propyl p-diethylaminobenzoate, and the like.

Examples of tertiary aromatic amines other than the alkyl p-dialkylaminobenzoate include 7-dimethylamino-4-methylcoumarin, N,N-dimethylaniline, N,N-dibenzylaniline, N,N-dimethyl-p-toluidine, N,N-diethyl-p-toluidine, N,N-bis(2-hydroxyethyl)-p-toluidine, N,N,2,4,6-pentamethylaniline, N,N,2,4-tetramethylaniline, N,N-diethyl-2,4,6-trimethylaniline, and the like.

The tertiary amine may be used alone or in combination with two or more kinds.

The first and/or second components may further contain a polymerization inhibitor, a photopolymerization initiator, a filler other than a basic filler, and the like.

Examples of the polymerization inhibitors include dibutyl hydroxytoluene (2,6-di-tert-butyl-p-cresol), 6-tert-butyl-2,4-xylenol, and the like. Two or more kinds of polymerization inhibitors may be used in combination.

Examples of the photopolymerization initiators include camphorquinone, phenylbis (2,4,6-trimethylbenzoyl) phosphineoxide, 2,4,6-trimethylbenzoyl diphenylphosphine, benzyl ketal, diacetyl ketal, benzyl dimethyl ketal, benzyl diethyl ketal, benzyl bis(2-methoxyethyl) ketal, 4,4'-dimethyl (benzyl dimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis(4-dimethylaminophenyl)ketone, 4,4'-bis(diethylamino)benzophenone, and the like. Two or more kinds of photopolymerization initiators may be used in combination.

Examples of fillers other than the basic filler include anhydrous silicic acid powder, fumed silica, alumina powder, glass powder (for example, barium glass powder, fluoroaluminosilicate glass powder), and the like. Two or more kinds of fillers may be used in combination.

The filler other than the basic filler may be treated with a surface treatment agent such as a silane coupling agent and the like.

EXAMPLES

Hereinafter, examples of the present invention will be described, but the present invention is not limited to the examples.

Examples 1 to 6, Comparative Examples 1 to 4

(Preparation of Paste 1)

Paste 1 was prepared by mixing a methacrylate free of an acid group, a methacrylate having an acid group, an organic peroxide, a filler, and a polymerization inhibitor according to the amounts [% by mass] indicated in Table 1.

The abbreviations indicated in Table 1 are as follows.
UDMA: di-2-methacryloyloxyethyl-2,2,4-trimethylhexamethylene dicarbamate
EBDMA: Ethoxylated bisphenol-A dimethacrylate
NPG: Neopentylglycol dimethacrylate
Bis-GMA: 2,2-bis[4-(3-methacryloxy-2-hydroxypropyl)] phenylpropane
HOMS: 2-methacryloyloxyethylsuccinic acid
MAA: Methacrylic acid
MDP: 10-methacryloyloxydecyldihydrogenphosphate
CHP: Cumene hydroperoxide
Filler 1: Barium glass powder G018-053 UF0.4 (manufactured by SCHOTT)
Filler 2: Aerosil R812 (hydrophobic fumed silica) (manufactured by Nippon Aerosil Co., Ltd.)
BHT: Dibutyl hydroxytoluene (2,6-di-tert-butyl-p-cresol)
(Preparation of Paste 2)

Paste 2 was prepared by mixing UDMA (15% by mass), EBDMA (15% by mass), and NPG (10% by mass) as a methacrylate free of an acid group; vanadyl acetylacetonate (0.05% by mass) as a vanadium compound; N-benzoyl thiourea (0.5% by mass) as a thiourea derivative; filler 1

(58.7% by mass) and filler 2 (0.5% by mass); ethyl p-dimethylaminobenzoate (0.1% by mass) as a tertiary amine; camphorquinone (0.05% by mass) and 2,4,6-trimethylbenzoyl diphenylphosphine oxide (0.05% by mass) as a photopolymerization initiator; and dibutyl hydroxytoluerie (0.05% by mass) as a polymerization inhibitor.

Next, the curability of pastes 1 and 2 (dental polymerizable compositions), storage stability and X-ray contrast of the cured products were evaluated.

(Curability)

The curability of the dental polymerizable composition was evaluated in accordance with ISO 4049:2019.

Specifically, paste 1 and paste 2 were kneaded in a mass ratio of 1:1, and then the kneaded paste was filled into a polyethylene tube having an inner diameter of 4 mm and a height of 6 mm to prepare a test piece. A thermocouple was then used to record the temperature change of the test piece and determine an initial setting time.

The criteria for curability of dental polymerizable compositions are as follows.

Excellent: Initial setting time is 4 minutes or more and less than 5 minutes.
Good: Initial setting time is 5 minutes or more and less than 7 minutes, or 3 minutes or more and less than 4 minutes.
Poor: Initial setting time is 7 minutes or more, or less than 3 minutes.

(Storage Stability)

Accelerated testing was performed to evaluate the storage stability of dental polymerizable compositions.

Specifically, the pastes 1 and 2 were stored at 60° C. for 7 days, and then a setting time was determined in the same manner as the initial setting time.

The criteria for storage stability of dental polymerizable compositions are as follows.

Excellent: A difference between the initial setting time and the setting time of the dental polymerizable composition is less than 3 minutes.
Good: A difference between the initial setting time and the setting time of the dental polymerizable composition is 3 minutes or more and less than 5 minutes.
Poor: A difference between the initial setting time and the setting time of the dental polymerizable composition is 5 minutes or more.

(X-Ray Contrast of Cured Products)

A X-ray contrast of the dental polymerizable composition was evaluated in accordance with ISO 4049:2019 as follows.

Paste 1 and Paste 2 were kneaded in a mass ratio of 1:1. A polyester sheet was then placed at the bottom of a fluoropolymer ring having an inner diameter of 15 mm and a thickness of 1 mm. The kneaded dental polymerizable composition was filled in the ring. Next, a polyester sheet was placed on top of the ring, and then the kneaded dental polymerizable composition was photocured in press-welded contact with a glass plate to obtain a test piece.

A digital X-ray apparatus was used to take simultaneous photographs of the test piece and an aluminum step plate, and the digital image files were transferred to a gray scale value analysis software to measure the average gray scale value of the test piece. Next, the gray scale value was measured in each step of the aluminum step plate. The gray scale value and thickness of each step of the aluminum step plate were then plotted to determine the relationship between the gray scale value and the aluminum thickness. The aluminum thickness corresponding to the gray scale value of the test piece was then determined.

The criteria for X-ray contrast of the cured product of the dental polymerizable composition are as follows.

Excellent: The thickness of the aluminum corresponding to the gray scale value of the test piece is 2.5 mm or more.
Good: The thickness of the aluminum corresponding to the gray scale value of the test piece is 1.5 mm or more and less than 2.5 mm.
Poor: The thickness of the aluminum corresponding to the gray scale value of the test piece is less than 1.5 mm.

Table 1 indicates the evaluation results of curability, storage stability, and X-ray contrast of the dental polymerizable compositions.

TABLE 1

| | | | Examples | | | | | |
|---|---|---|---|---|---|---|---|---|
| | | | 1 | 2 | 3 | 4 | 5 | 6 |
| Paste 1 | Methacrylate without an acid group | UDMA | 20 | 20 | 20 | 20 | 20 | 20 |
| | | EBDMA | 10 | 10 | 10 | 10 | 10 | 10 |
| | | NPG | 10 | 10 | 10 | 10 | 10 | 10 |
| | | Bis-GMA | 5 | 5 | 5 | 5 | 5 | 5 |
| | Methacrylate having an acid group | HOMS | 0.5 | 1 | 1.5 | | | |
| | | MAA | | | | 0.5 | 1 | 1.5 |
| | | MDP | | | | | | |
| | Organic peroxide | CHP | 1 | 1 | 1 | 1 | 1 | 1 |
| | Filler | Filler 1 | 52.9 | 52.4 | 51.9 | 52.9 | 52.4 | 51.9 |
| | | Filler 2 | 0.5 | 0.5 | 0.5 | 0.5 | 0.5 | 0.5 |
| | Polymerization inhibitor | BHT | 0.1 | 0.1 | 0.1 | 0.1 | 0.1 | 0.1 |
| | Total | | 100 | 100 | 100 | 100 | 100 | 100 |
| Curability | Initial setting time | | 5'35" | 4'25" | 3'30" | 4'15" | 3'40" | 3'05" |
| | Evaluation | | Good | Excellent | Good | Excellent | Good | Good |
| Storage stability | Setting time | | 8'05" | 6'20" | 5'05" | 6'05" | 4'40" | 3'55" |
| | Evaluation | | Excellent | Excellent | Excellent | Excellent | Excellent | Excellent |
| X-ray contrast | Thickness of aluminum corresponding to gray scale value of test piece [mm] | | 2.8 | 2.8 | 2.8 | 2.8 | 2.8 | 2.8 |
| | Evaluation | | Excellent | Excellent | Excellent | Excellent | Excellent | Excellent |

TABLE 1-continued

|  |  |  | Comparative Examples | | | |
|---|---|---|---|---|---|---|
|  |  |  | 1 | 2 | 3 | 4 |
| Paste 1 | Methacrylate without an acid group | UDMA | 20 | 20 | 20 | 20 |
|  |  | EBDMA | 10 | 10 | 10 | 10 |
|  |  | NPG | 10 | 10 | 10 | 10 |
|  |  | Bis-GMA | 5 | 5 | 5 | 5 |
|  | Methacrylate having an acid group | HOMS |  |  |  |  |
|  |  | MAA |  |  |  |  |
|  |  | MDP |  | 0.5 | 1 | 1.5 |
|  | Organic peroxide | CHP | 1 | 1 | 1 | 1 |
|  | Filler | Filler 1 | 53.4 | 52.9 | 52.4 | 51.9 |
|  |  | Filler 2 | 0.5 | 0.5 | 0.5 | 0.5 |
|  | Polymerization inhibitor | BHT | 0.1 | 0.1 | 0.1 | 0.1 |
|  |  | Total | 100 | 100 | 100 | 100 |
| Curability | Initial setting time |  | 9'15" | 6'15" | 5'20" | 4'35" |
|  | Evaluation |  | Poor | Good | Good | Excellent |
| Storage stability | Setting time |  | 12'20" | 11'15" | 10'30" | 10'15" |
|  | Evaluation |  | Good | Poor | Poor | Poor |
| X-ray contrast | Thickess of aluminum corresponding to gray scale value of test piece [mm] |  | 2.8 | 2.8 | 2.8 | 2.8 |
|  | Evaluation |  | Excellent | Excellent | Excellent | Excellent |

From Table 1, it is apparent that the dental polymerizable compositions of Examples 1 to 6 have high curability and storage stability, and have high X-ray contrast of the cured products.

In contrast, the dental polymerizable composition of Comparative Example 1 has paste 1 that does not contain a (meth)acrylate having an acid group. Accordingly, the dental polymerizable composition of Comparative Example 1 has low curability.

The dental polymerizable compositions of Comparative Examples 2 to 4 also have paste 1 which does not contain a (meth)acrylate having a carboxyl group but which contains a (meth)acrylate having a phosphate group. Accordingly, the dental polymerizable compositions of Comparative Examples 2 to 4 have low storage stability.

What is claimed is:

1. A dental polymerizable composition comprising:
a first component containing a (meth)acrylate free of an acid group, a (meth)acrylate having a carboxyl group, a basic filler, and an organic peroxide; and
a second component containing a (meth)acrylate free of an acid group, a vanadium compound, and a thiourea derivative,
wherein a content of the (meth)acrylate having the carboxyl group is 0.1 to 0.9% by mass.

2. The dental polymerizable composition according to claim 1, wherein the second component further comprises a basic filler.

3. The dental polymerizable composition according to claim 1, wherein the basic filler is barium glass powder.

4. The dental polymerizable composition according to claim 1, wherein a content of the basic filler in the dental polymerizable composition is 4 to 90% by mass.

5. A dental polymerizable composition comprising:
a first component containing a (meth)acrylate free of an acid group, a (meth)acrylate having a carboxyl group, a basic filler, and an organic peroxide; and
a second component containing a (meth)acrylate free of an acid group, a vanadium compound, and a thiourea derivative,
wherein the composition excludes a (meth)acrylate having a phosphate group.

6. The dental polymerizable composition according to claim 5, wherein a content of the (meth)acrylate having the carboxyl group is 0.1 to 0.9% by mass.

7. The dental polymerizable composition according to claim 5, wherein the basic filler is barium glass powder.

8. The dental polymerizable composition according to claim 5, wherein the second component further comprises a basic filler.

9. The dental polymerizable composition according to claim 5, wherein a content of the basic filler in the dental polymerizable composition is 4 to 90% by mass.

10. A dental polymerizable composition comprising:
a first component containing a (meth)acrylate free of an acid group, a (meth)acrylate having a carboxyl group, barium glass powder, and an organic peroxide; and
a second component containing a (meth)acrylate free of an acid group, a vanadium compound, and a thiourea derivative wherein a content of the (meth)acrylate having the carboxylic group is 0.1 to 0.9% by mass.

11. The dental polymerizable composition according to claim 10, wherein the second component further comprises a basic filler.

12. The dental polymerizable composition according to claim 10, wherein a content of the basic filler in the dental polymerizable composition is 4 to 90% by mass.

* * * * *